United States Patent
Fernandez

(10) Patent No.: US 11,833,092 B2
(45) Date of Patent: Dec. 5, 2023

(54) DEVICE AND METHOD FOR MOVING BEDRIDDEN PATIENTS

(71) Applicant: B. B. G. E. Z. P. P., LLC, New York, NY (US)

(72) Inventor: Lisette Fernandez, New York, NY (US)

(73) Assignee: B. B. G. E. Z. P. P. LLC, New York, NY (US)

( * ) Notice: Subject to any disclaimer, the term of this patent is extended or adjusted under 35 U.S.C. 154(b) by 174 days.

(21) Appl. No.: 16/602,525

(22) Filed: Oct. 23, 2019

(65) Prior Publication Data

US 2022/0000691 A1  Jan. 6, 2022

Related U.S. Application Data

(60) Provisional application No. 62/919,521, filed on Mar. 15, 2019.

(51) Int. Cl.
*A61G 7/10* (2006.01)

(52) U.S. Cl.
CPC .......... *A61G 7/1023* (2013.01); *A61G 7/103* (2013.01)

(58) Field of Classification Search
CPC .... A61G 7/1023; A61G 7/1026; A61G 7/103; A61G 7/1036; A61G 7/1025; A47C 20/027; A47C 20/021; A47C 20/026; A47C 20/023; A47C 20/02; A47C 17/045; A47B 91/06
See application file for complete search history.

(56) References Cited

U.S. PATENT DOCUMENTS

| | | | | | |
|---|---|---|---|---|---|
| 433,905 | A | * | 8/1890 | Müller | A47C 21/006 5/694 |
| 2,404,734 | A | * | 7/1946 | Lenahan | A61G 7/1046 5/81.1 R |
| 3,167,789 | A | * | 2/1965 | Wicks | A61G 7/1046 5/81.1 HS |
| 3,512,189 | A | * | 5/1970 | Swanson | A61G 7/103 5/630 |
| 3,742,526 | A | * | 7/1973 | Lillard | A47C 17/045 5/12.1 |
| 4,012,799 | A | * | 3/1977 | Rutherford | A61G 7/103 5/81.1 R |
| 4,361,918 | A | * | 12/1982 | Roisaeth | A61G 7/1038 280/47.21 |
| 4,518,203 | A | * | 5/1985 | White | A47C 17/045 297/108 |
| 4,686,719 | A | * | 8/1987 | Johnson | A61G 7/1021 180/125 |

(Continued)

OTHER PUBLICATIONS

"Elastomers and Rubbers—What's the Difference"—Global Elastomeric Products, Inc. <https://www.globaleee.com/global-news/-history/elastomers-rubbers-difference> (Year: 2016).*

*Primary Examiner* — David R Hare

(57) ABSTRACT

A system for repositioning patients including a plate assembly and a strap assembly. The system includes at least two plates including a first portion and a second portion mounted to the first portion and configured to receive a strap assembly therein. A user utilizes the system for repositioning patients every 2-3 hours per healthcare industry standards of care to prevent the patient from contracting bed sores.

18 Claims, 7 Drawing Sheets

(56) References Cited

U.S. PATENT DOCUMENTS

| | | | | |
|---|---|---|---|---|
| 4,716,607 A * | 1/1988 | Johansson | A61G 7/103 | 5/81.1 T |
| 4,768,239 A * | 9/1988 | Pauley | A61G 7/1003 | 4/564.1 |
| 4,777,678 A * | 10/1988 | Moore | A47C 20/027 | 606/240 |
| 4,793,008 A * | 12/1988 | Johansson | A61G 7/103 | 5/81.1 T |
| 5,038,425 A * | 8/1991 | Merry | A61G 7/1015 | 5/83.1 |
| 5,271,110 A * | 12/1993 | Newman | A61G 7/103 | 5/625 |
| 5,448,790 A * | 9/1995 | Saro | A47C 17/045 | 5/427 |
| 5,577,281 A * | 11/1996 | Mital | A61G 7/103 | 5/625 |
| 5,664,271 A * | 9/1997 | Bellavance | A47C 20/021 | 5/630 |
| 5,966,754 A * | 10/1999 | Schuster | A61G 7/103 | 5/81.1 R |
| 5,997,491 A * | 12/1999 | Harris | A47C 20/021 | 128/882 |
| 6,009,873 A * | 1/2000 | Neviaser | A47C 20/027 | 128/845 |
| 6,182,311 B1 * | 2/2001 | Buchanan | A47C 20/021 | 128/845 |
| 6,349,432 B1 * | 2/2002 | Scordato | A61G 5/006 | 5/81.1 HS |
| 6,795,990 B1 * | 9/2004 | Hutchinson | A47C 20/021 | 5/490 |
| 7,003,803 B1 * | 2/2006 | Lyden | A41D 13/0153 | 2/22 |
| 7,018,351 B1 * | 3/2006 | Iglesias | A61F 5/0111 | 128/882 |
| 7,020,918 B1 * | 4/2006 | Tinsley | A47C 16/00 | 5/630 |
| 7,427,243 B2 * | 9/2008 | Sullivan | A63B 37/0003 | 473/378 |
| 8,096,008 B1 * | 1/2012 | Phillips | A61G 1/04 | 5/626 |
| 8,973,191 B1 * | 3/2015 | Kvitek | A47G 9/10 | 5/640 |
| 9,144,318 B1 * | 9/2015 | Lagier | A47C 15/006 | |
| D786,143 S * | 5/2017 | Couch | D12/128 | |
| 10,321,764 B2 * | 6/2019 | Caluwaert | A47C 1/146 | |
| 10,729,605 B1 * | 8/2020 | Chinake | A61G 7/001 | |
| 10,765,580 B1 * | 9/2020 | Augustine | B32B 7/12 | |
| 2006/0282946 A1 * | 12/2006 | Meyer | A61G 7/103 | 5/81.1 HS |
| 2007/0056096 A1 * | 3/2007 | Assink | A47C 27/14 | 5/81.1 HS |
| 2008/0178390 A1 * | 7/2008 | DuDonis | A47C 20/021 | 5/632 |
| 2009/0004452 A1 * | 1/2009 | Assink | A61G 1/01 | 428/220 |
| 2009/0307839 A1 * | 12/2009 | Wilson | A61G 7/103 | 5/81.1 HS |
| 2010/0199423 A1 * | 8/2010 | Kraemer | A61G 7/103 | 5/81.1 HS |
| 2011/0271444 A1 * | 11/2011 | Davis | A61G 7/1026 | 5/81.1 R |
| 2012/0255565 A1 * | 10/2012 | Hursh | A61G 1/00 | 128/870 |
| 2015/0035333 A1 * | 2/2015 | Schy | A61G 7/1019 | 297/331 |
| 2017/0000667 A1 * | 1/2017 | Olivo | A61G 1/013 | |
| 2017/0119608 A1 * | 5/2017 | Rigoni | A61G 7/001 | |
| 2018/0036190 A1 * | 2/2018 | Glibert | A61G 7/1015 | |
| 2018/0055704 A1 * | 3/2018 | Mlungwana | A61G 7/1088 | |
| 2018/0153319 A1 * | 6/2018 | Artis | A47G 9/1045 | |
| 2018/0344552 A1 * | 12/2018 | Kamara | A47C 31/10 | |
| 2019/0046382 A1 * | 2/2019 | Pigazzi | A61G 13/1285 | |
| 2019/0142669 A1 * | 5/2019 | Tobias | B32B 3/266 | 5/81.1 R |
| 2019/0201263 A1 * | 7/2019 | Depauw | A61G 7/1036 | |

\* cited by examiner

DEVICE AND METHOD FOR MOVING BEDRIDDEN PATIENTS

RELATED APPLICATIONS

The present application claims priority of U.S. Provisional Patent Application Ser. No. 62/919,521, filed on Mar. 15, 2019, which is hereby incorporated by reference.

FIELD OF THE INVENTION

The present invention relates to a device and method for repositioning patients who are confined to a bed. More particularly, the invention relates to a device which enables a caregiver to reposition a patient with less effort and a reduced risk of strain or repetitive use injury.

BACKGROUND

There is a class of hospital, rehab, and nursing home patients who are comatose, quadriplegic, or otherwise immobilized and thus temporarily or permanently bedridden. A major problem for such patients is a form of skin inflammation known as decubitus, in which the skin breaks down due to constant compression against the surface of the bed. Ulcers, known as bed sores or pressure sores, are prone to infection and can progress to deep, life-threatening wounds. Decubitus can be prevented if the patient is repositioned regularly, so that pressure on any given portion of the skin is relieved for a time. Individuals responsible for the care of such patients are required to reposition them every 2 to 3 hours.

Immobilized patients are prone to obesity, due to the lack of exercise, and it is not uncommon for health care workers to be confronted with the task of repositioning a patient of any weight. This is a physically demanding task, and the worker performing it is at risk of both acute and repetitive strain injuries. Several systems for repositioning patients have been designed in the past.

U.S. Pat. No. 7,818,836 discloses a repositioning device for patients, the device having a pad member with at least two sets of turning members attached on its sides and at least one line of perforations or the like extending laterally across the pad member such that the lower portion of the pad member can be separated from the remainder portion if the lower portion becomes soiled. The disclosed device is essentially a modified bedsheet, and does not provide for easy sliding of the patient relative to the sheet.

The prior art provides a number of more or less complicated features that fail to solve the problem in an efficient and economical way. There remains a need for an easy and efficient system to reposition a patient that does not require great physical effort by a user.

SUMMARY OF THE INVENTION

It is one of the objects of the present invention to provide a system for repositioning patients that facilitating the process of turning and positioning patients every two to three hours per industry standards of care for hospitals, home care agencies, long term care, and rehabilitation facilities.

It is another object of this invention to provide a system for repositioning patients that creates ease of movement while positioning the patient by reducing the shearing force created by the patient's weight.

It is still another object of the present invention to provide a system for repositioning patients that bears the weight of the patient, reducing the physical stress distributed to the caregiver's hands and back thereby lessening the overall physical exertion and occurrence of repetitive use injuries.

It is yet another object of this invention to provide such a device that is inexpensive to implement and maintain while retaining its effectiveness.

The invention provides a plate assembly, the lower surface of which has a low coefficient of friction. The upper surface has a very high coefficient of friction. The plate has an attached strap, which can be used to transfer the patient's weight to the plate. With one such plate under a hip, and a second such plate under a shoulder, the majority of the patient's weight is then borne upon the plates, and by pulling on the straps it is possible to easily slide the patient around on the surface of the bed. The patient is then rolled onto his or her side and off of the plate.

DETAILED DESCRIPTION OF THE INVENTION

Figure 1:
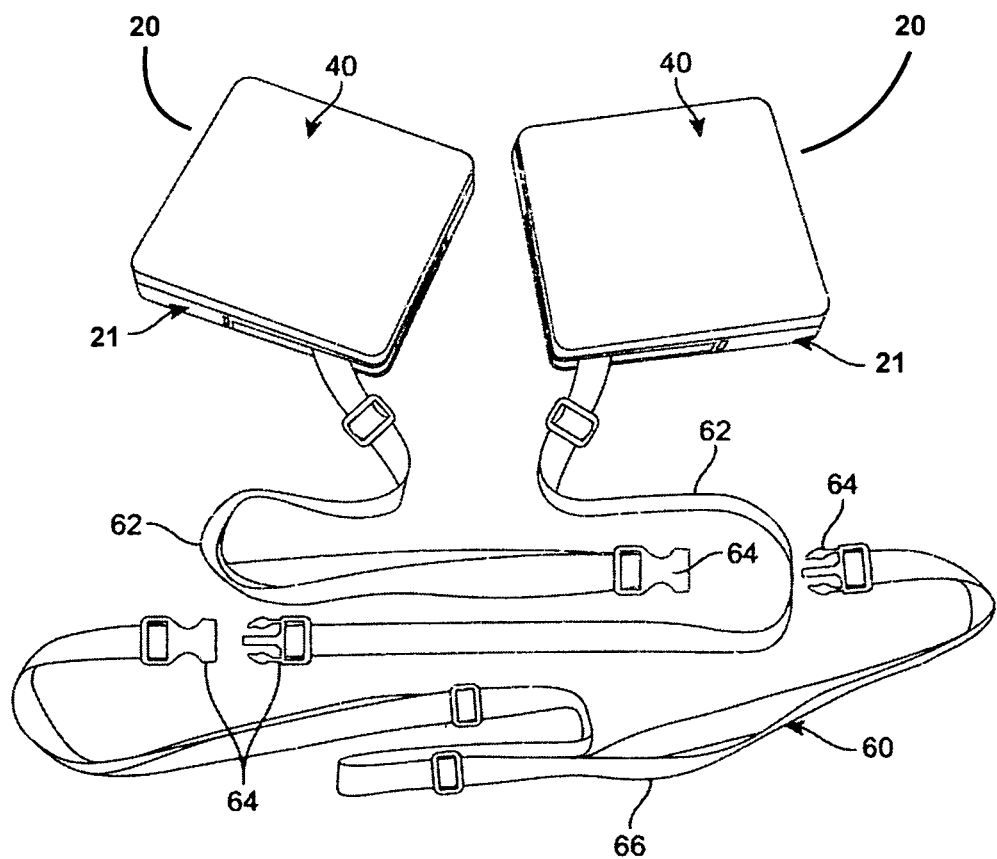
FIG. 1 is an isometric view of a pair of devices for repositioning patients, that represent one embodiment of the present invention.
Figure 2:
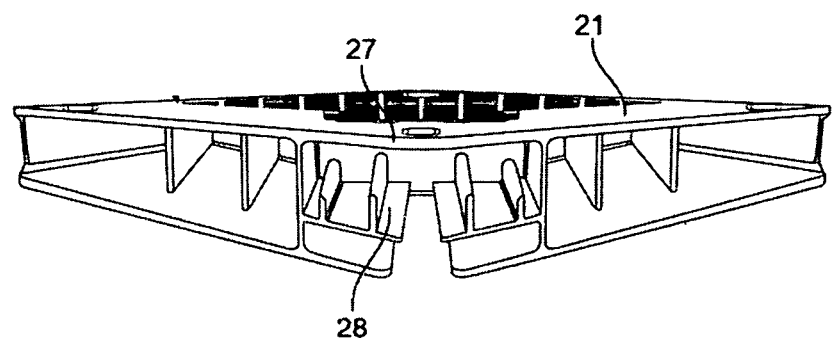
FIG. 2 illustrates a rear view of one of the devices of FIG. 1.
Figure 3:
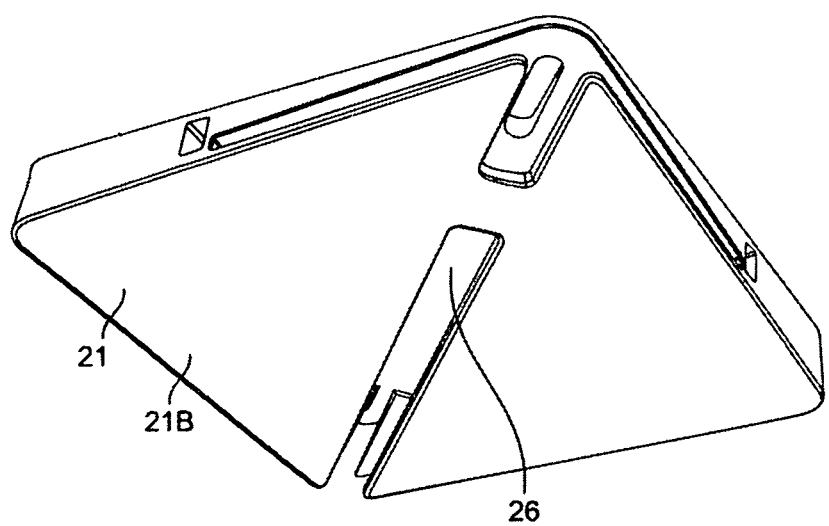
FIG. 3 represents a bottom view of one of the devices of FIG. 1.

In general terms, the invention provides a plate having an upper surface with a very high coefficient of friction, a lower surface having a very low coefficient of friction. Generally, these two surfaces are provided by assembling two separate sections, made of two different materials, into a plate of the invention. Each plate has an attached strap. Two such plates, with their straps, form a system for moving patients. The plates are preferably provided in the form of a kit comprising two plates and their associated straps. Preferably, the system and kit further comprise a connecting strap.

As illustrated in the embodiment shown in the drawings, the lower section may be formed with a waffle or honeycomb structure, in order to reduce weight while maintaining strength and rigidity. The upper section may be similarly constructed, to reduce weight and increase the compressibility of the section.

The upper and lower sections are attached to each other by any of several means, alone or in combination. Suitable means include but are not limited to adhesives, locking tabs and slots, and appropriately recessed screws and rivets. The attachment may be permanent in nature, or reversible if occasional replacement of the upper elastomeric section is desired. The only requirement is that the attachment be sturdy enough to prevent detachment of the sections during routine use.

Referring now to the drawings, a particular embodiment of the invention's system for repositioning patients is illustrated.

The plate system includes at least two plates 20, each plate comprising an upper section or cover assembly 40 and a lower section 21 having a top surface 21A and a bottom surface 21B. The plate section 21 may be made of any rigid structural material such as plastic, metal, carbon fiber, and the like, provided that the bottom surface is smooth and thus has a low coefficient of friction. The coefficient of friction, relative to a cotton/polyester bedsheet, is preferably less than 1, and more preferably less than 0.5. In the illustrated embodiment, two plate 21 is made of a strong thermoplastic material such as ABS or nylon. It should be understood that any suitable shapes may be used for the plates. In the illustrated embodiment, the plate 21 is of a suitable shape to comfortably fit underneath the hip and shoulder portion of a patient to aid a user in repositioning the patient. The plate 21 has a top surface 21A having top openings 22 thereon. In the present embodiment, top openings 22 are of an oval shape and disposed on each corner of top surface 21A. It should be understood that additional embodiments may be provided wherein top openings 22 may be given in additional suitable shapes. In this embodiment, plate 21 has a waffled portion 23 disposed on top surface 21A. Waffled portion 23 includes square shaped rectangular indentions disposed partially on top surface 21A. In alternative embodiments, a honeycomb or other pattern may be employed. The waffle or honeycomb construction removes material to save weight, with little loss in strength. Waffled portion 23 provides additional support for cover assembly 40 mounted on plate 21. The plate 21 further features sidewall openings 24. Sidewall openings 24 are disposed on sidewalls 25 of the plate 21. In the present embodiment sidewall openings 24 cooperate with the shape of the corners of two plates 21. Additionally, sidewall openings 24 are configured to receive strap assembly 40 therethrough, so that the user can adjust the strap to any needed position while the plate is immobilized beneath the patient. First portion 23 also includes a bottom channel 26 located on bottom surface 21B of two plates 21. In one embodiment, bottom channel 26 extends diagonally along bottom surface 21B of plate 21. Additionally, bottom channel 26 provides a necessary opening to allow strap assembly 60 to freely maneuver therein. Plate 21 further features a rear edge 27 having a rear edge opening 28. In one embodiment, rear edge opening 28 receives strap assembly 60 therethrough.

Cover assembly 40 includes cover 42. Cover 42 is made of a suitable elastomeric material such as a urethane, silicone or rubber polymer. Suitable materials include, but are not limited to, soft silicones' and thermal plastic urethane (TPU). Alternatively, a fabric-covered cushion may serve as the upper surface of the cover assembly, so long as the necessary coefficient of friction is provided. In a preferred embodiment of the present invention cover 42 has a high coefficient of friction, relative to a cotton/polyester bedsheet, in excess of 1.0 and preferably in excess of 1.5, more preferably in excess of 2.0. Cover 42 preferably features protrusions 44 located on a bottom side of covers, which aid in the secure attachment to the lower portion of the plate.

In an embodiment of the present invention, protrusions 44 are complimentary to the shape of top openings 22. Cover 42 is mounted on the top side 21A of plate 21. Protrusions 44 of cover 42 are inserted into the top openings 22 of plate 21. This prevents the cover and lower section from sliding relative to one another when the patient is moved.

Figure 4:
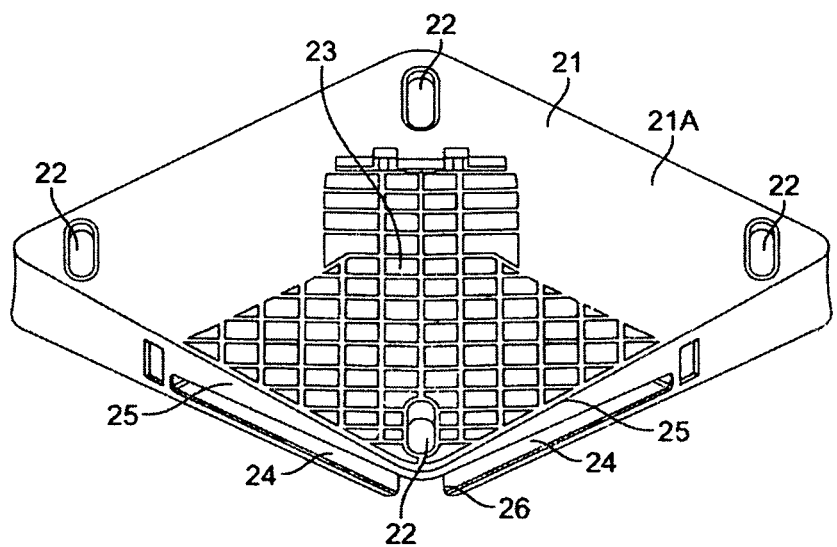
FIG. 4 shows an isometric view of one of the devices of FIG. 1.
Figure 5:
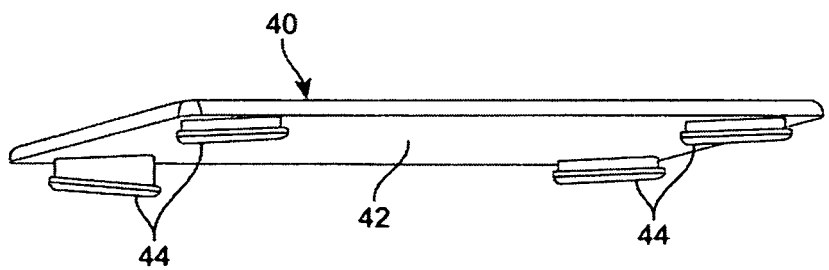
FIG. 5 is an isometric view of the underside of the cover assembly.
Figure 6:
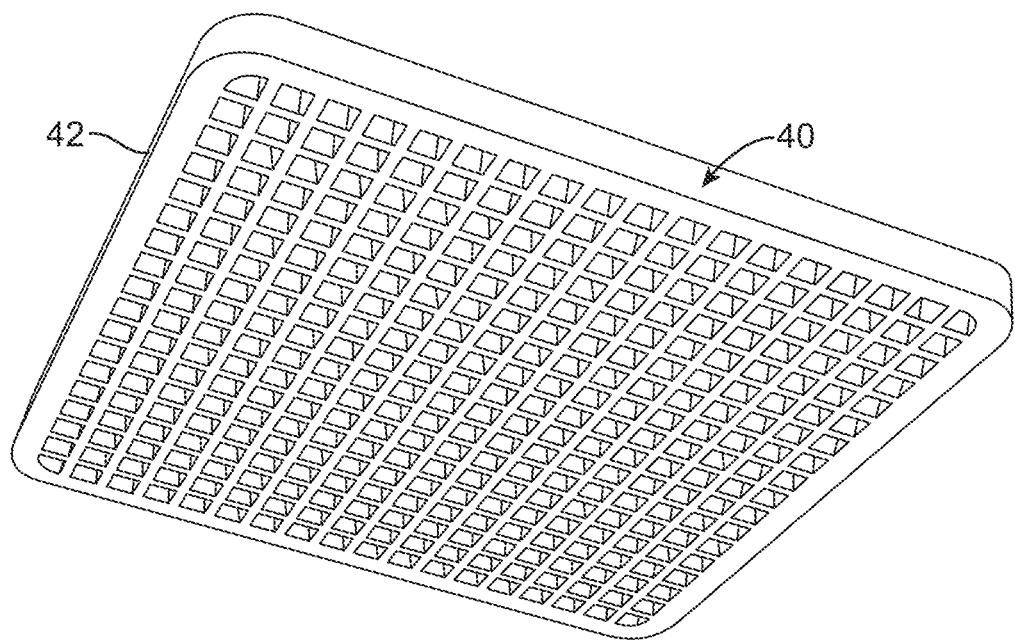
FIG. 6 is an isometric view of the underside of a second, alternative embodiment of the cover assembly.
Figure 7:
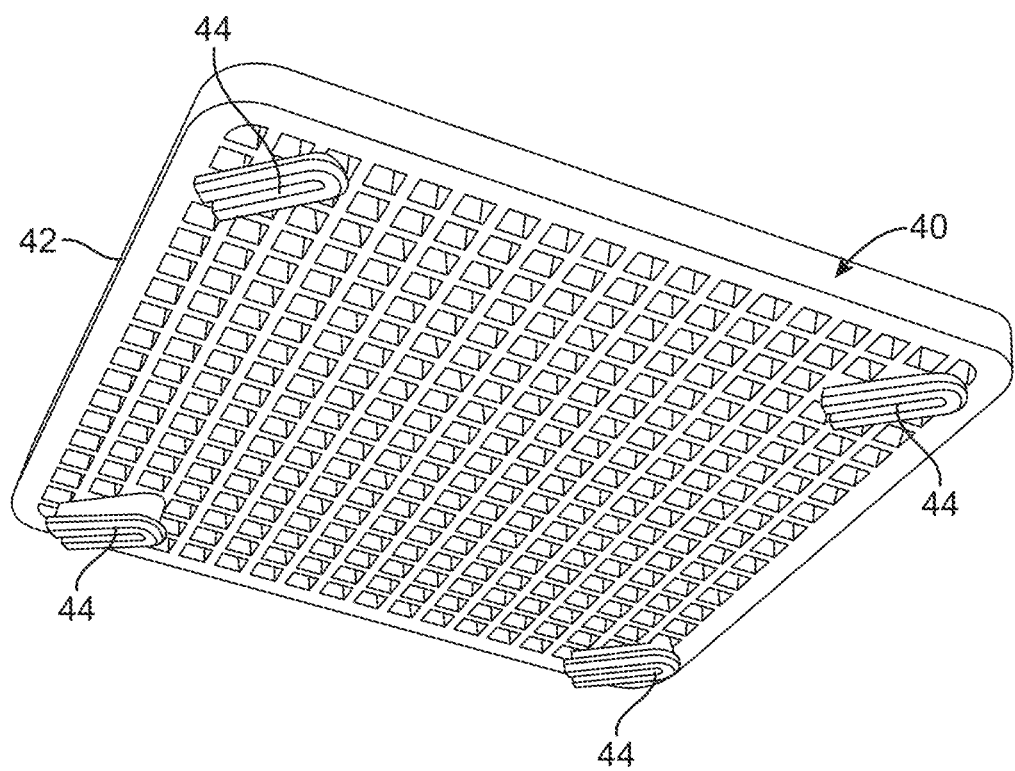
FIG. 7 is an isometric view of the underside of a third embodiment of the cover assembly.
Figure 8:
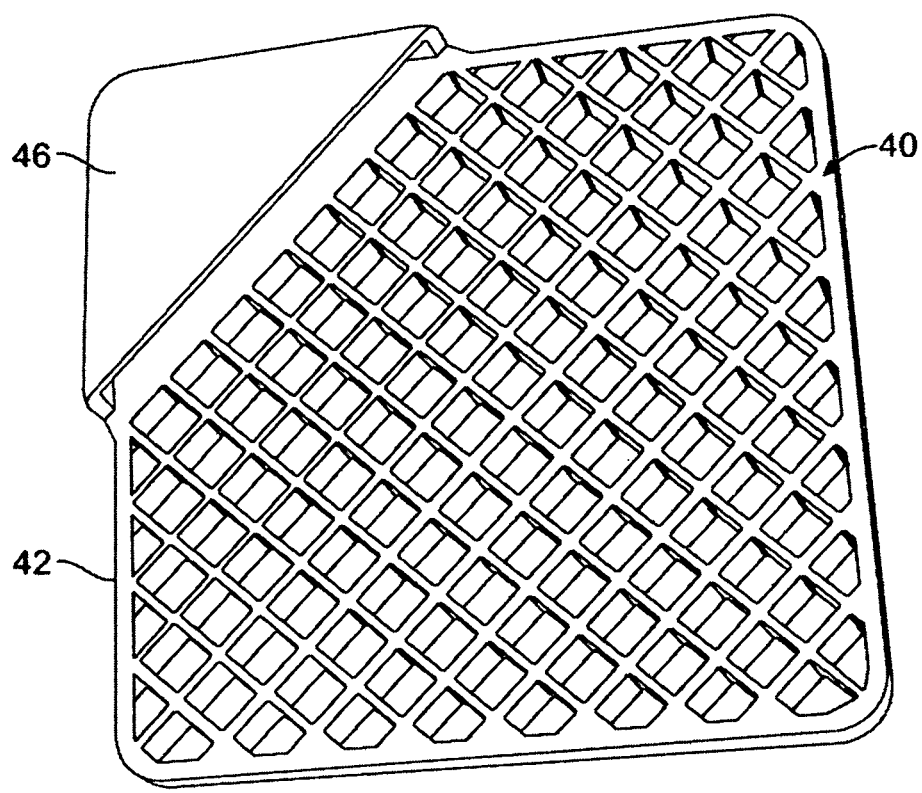
FIG. 8 is an isometric view of the underside of a fourth embodiment of the cover assembly.
Figure 9:
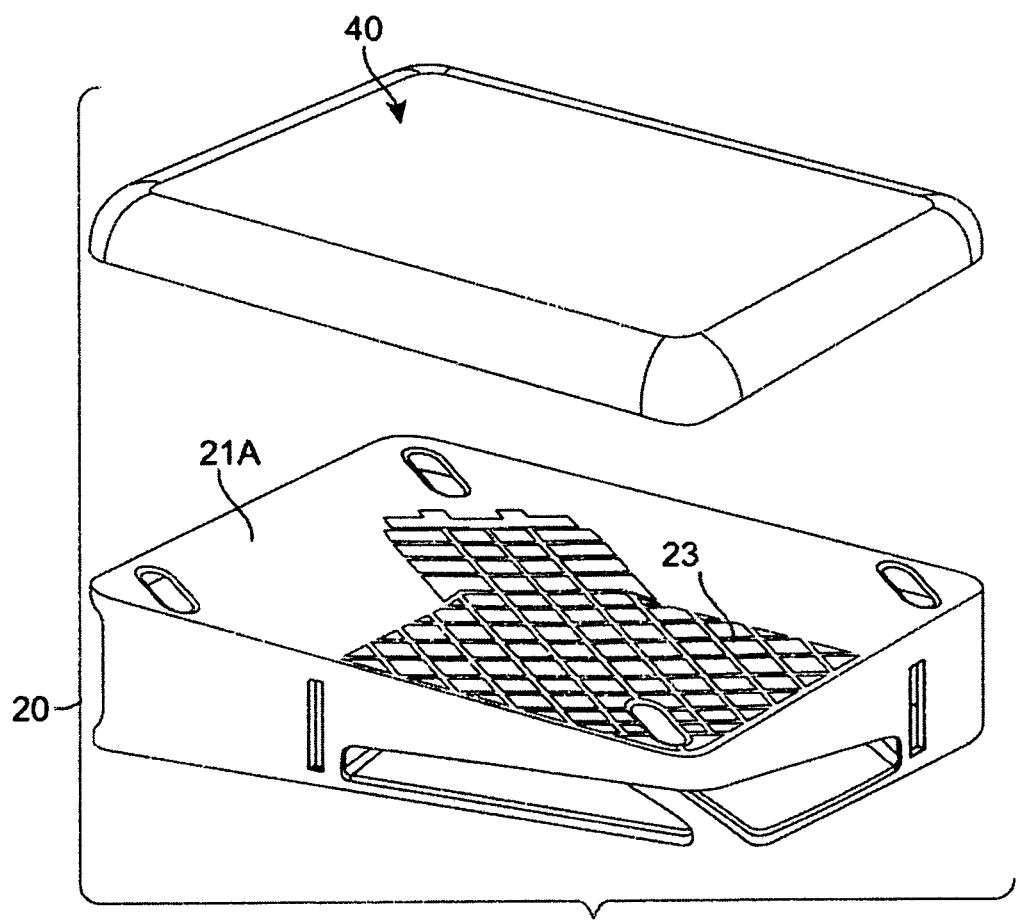
FIG. 9 is a representation of an exploded view of one of the plates of FIG. 1.
Figure 10:
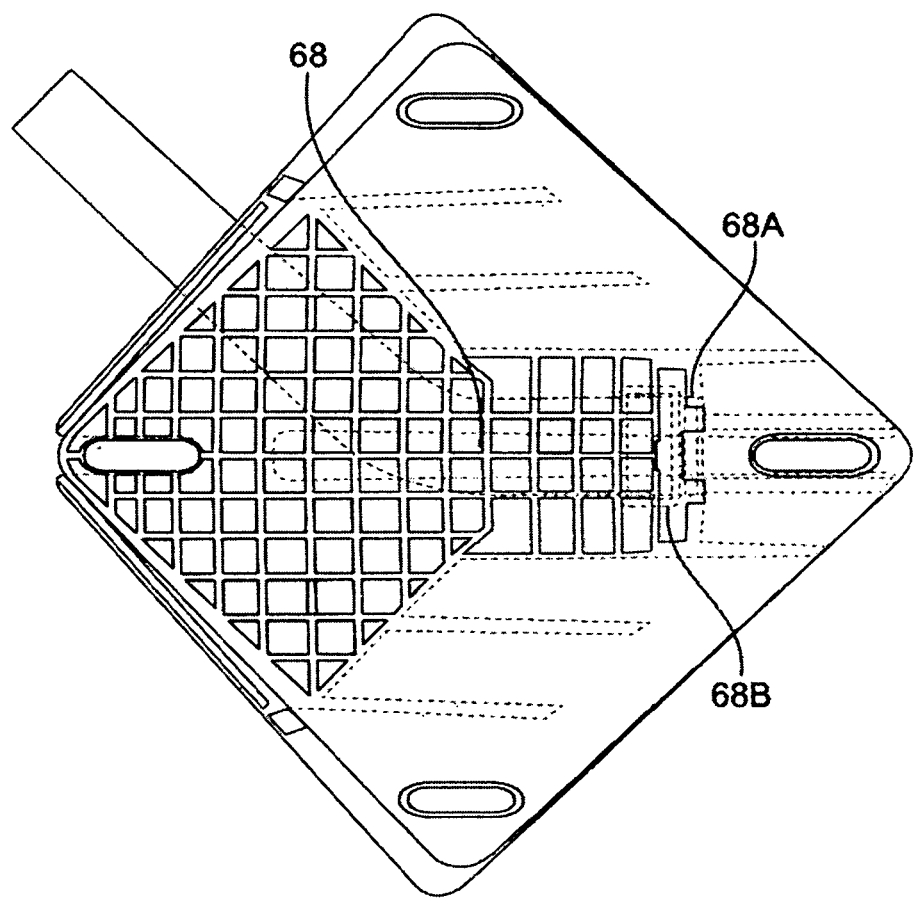
FIG. 10 shows top view of the lower section of one of the plates of FIG. 1.
Figure 11:
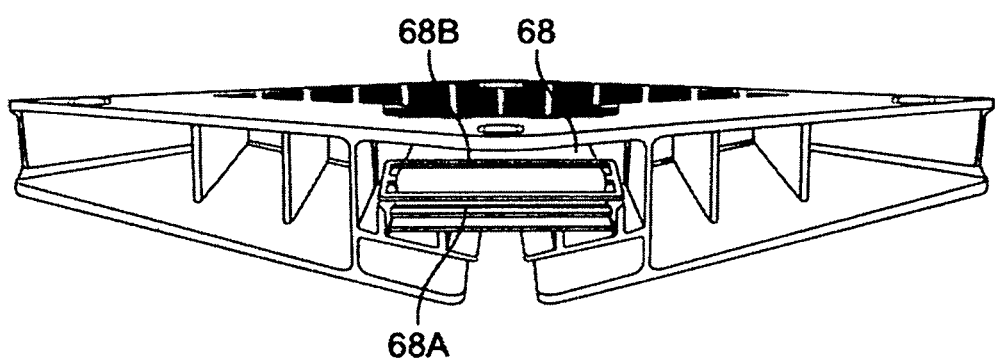
FIG. 11 illustrates a rear view of the lower section of one of the plates of FIG. 1.

It should be understood that additional embodiments of cover 42 may fall under the scope of the invention. In FIG. 4 an additional embodiment of cover 42 is further provided with a waffled portion encompassing the entire bottom surface of cover 42. FIG. 5 shows yet another embodiment of the present invention, a combination of protrusions and a waffled portion may be provided on a bottom surface of cover 42. In yet another embodiment of the present invention, FIG. 6 shows a cover 42 provided with a pocket 46 configured on one of the corners of cover 42. Pocket 46 will be received through sidewall openings 24 of plate 21 to securely mount cover 42 thereon. These embodiments are within the scope of the invention.

Strap assembly 60 includes straps 62 and buckles 64. In the present invention, straps 62 pass through sidewall openings 24 of two plates 21 and are securely mounted therethrough. In one embodiment, the ends of straps 62 may include buckles 64 mounted thereon. Buckles 64 aid a user in securing said straps together if needed by the user in repositioning a patient. In the present invention, straps 62 are adjustable using the hand of a user. Straps 62 may be made of a suitable material configured to aid a user in pulling a patient. Such a material may include a sturdy cloth material or the like. Strap assembly 60 further includes a connecting strap 66 further having buckles 64 configured to aid a user in connecting two plates 21 having straps 62 thereon. In the present embodiment a user utilizes connecting strap 66 to connect two plates 21 together to create one system. Strap assembly 60 further includes a rear strap 68 located on rear edge 27 of each of two plates 21. In one embodiment, rear strap 68 is fed through two plates 21 and comes out of rear edge opening 28 of rear edge 27. Rear strap 68 further includes a knot 68A and a tri-glide buckle 68B. In one embodiment, as a user pulls on straps 62, knot 68A and tri-glide buckle 68B lock within rear edge opening 28. As a result, a secure locking mechanism is created to lock strap 62 within plate 21.

The system for repositioning a patient may be utilized in a variety of ways. For example, two plates may be positioned underneath the hips of a patient to aid a user in pulling the patient higher on a bed with the use of connecting strap 66. One of the plates is then moved beneath the opposite shoulder of the patient. The straps are then used to partially lift the patient, transferring most or all of the weight to the plates. The straps can then be used to pull the patient to the side of the bed, taking advantage of the low coefficient of friction of the lower surfaces of the plates. Once the patient is near the side of the bed, a user may then further utilize the straps to roll the patient further, onto his or her side, and off of the plates. This process requires much less effort than is required in the absence of the plates of the invention.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A plate system for repositioning a patient, comprising at least two separate plates, each plate configured to be separately placeable under the patient's shoulder or hip, and each plate having an upper section having a high coefficient of friction, affixed to a lower section having a low coefficient of friction, and a strap attached to the lower section of each plate, the strap configured to attach and pass through a sidewall opening located on a vertically oriented sidewall of each plate which permits the position of each strap to be adjusted while each plate is positioned underneath a patient.

2. The plate system according to claim 1, wherein the upper section is made of an elastomeric material, and the lower section is formed from a rigid thermoplastic.

3. The plate system according to claim 2, wherein the elastomeric material is a silicone polymer or a thermal plastic urethane.

4. The plate system according to claim 1, wherein the upper section is affixed to the lower section by means of an adhesive.

5. The plate system according to claim 2, wherein the upper section is affixed to the lower section by means of an adhesive.

6. The plate system according to claim 3, wherein the upper section is affixed to the lower section by means of an adhesive.

7. The plate system according to claim 1, wherein the upper section is reversibly affixed to the lower section.

8. The plate system according to claim 2, wherein the upper section is reversibly affixed to the lower section.

9. The plate system according to claim 3, wherein the upper section is reversibly affixed to the lower section.

10. The plate system according to claim 1, further comprising a connecting strap adapted to connect the straps attached to the separate plates.

11. The plate system according to claim 2, further comprising a connecting strap adapted to connect the straps attached to the separate plates.

12. The plate system according to claim 3, further comprising a connecting strap adapted to connect the straps attached to the separate plates.

13. The plate system according to claim 4, further comprising a connecting strap adapted to connect the straps attached to the separate plates.

14. The plate system according to claim 5, further comprising a connecting strap adapted to connect the straps attached to the separate plates.

15. The plate system according to claim 6, further comprising a connecting strap adapted to connect the straps attached to the separate plates.

16. The plate system according to claim 7, further comprising a connecting strap adapted to connect the straps attached to the separate plates.

17. The plate system according to claim 8, further comprising a connecting strap adapted to connect the straps attached to the separate plates.

18. The plate system according to claim 9, further comprising a connecting strap adapted to connect the straps attached to the separate plates.

* * * * *